United States Patent [19]

Banks et al.

[11] Patent Number: 5,364,367
[45] Date of Patent: Nov. 15, 1994

[54] CANNULA ANCHOR

[75] Inventors: Thomas F. Banks; Claude Vidal, both of Santa Barbara, Calif.; Randall L. Knoll, Stillwater, Minn.; Russell J. Redmond, Goleta, Calif.

[73] Assignee: Minnesota Mining and Manufacturing Company, St. Paul, Minn.

[21] Appl. No.: 55,820

[22] Filed: Apr. 30, 1993

[51] Int. Cl.$^5$ ............................................. A61M 5/32
[52] U.S. Cl. .................... 604/174; 604/180; 128/DIG. 26
[58] Field of Search ............ 604/174, 178, 180; 128/DIG. 6, DIG. 26, 640

[56] References Cited

U.S. PATENT DOCUMENTS

| | | |
|---|---|---|
| 2,908,269 | 10/1959 | Cheng .................. 128/DIG. 26 X |
| 3,192,589 | 7/1965 | Pearson . |
| 3,353,663 | 11/1967 | Kayser et al. . |
| 3,408,705 | 11/1968 | Kayser et al. . |
| 3,487,837 | 1/1970 | Petersen ........................ 604/180 |
| 3,783,876 | 1/1974 | Dye ............................... 604/180 |
| 3,860,006 | 1/1975 | Patel ............................. 128/347 |
| 4,249,529 | 2/1981 | Nestor et al. ........... 128/DIG. 26 X |
| 4,473,067 | 9/1984 | Schiff ............................. 128/1 D |
| 4,519,793 | 5/1985 | Galindo ....................... 604/180 |
| 4,521,938 | 6/1985 | Kupcikevicius ................. 17/49 |
| 4,534,762 | 8/1985 | Heyer ...................... 128/DIG. 26 |
| 4,579,120 | 4/1986 | MacGregor .................. 604/174 |
| 4,593,681 | 6/1986 | Soni ................................. 128/4 |
| 4,598,004 | 7/1986 | Heinecke ...................... 428/40 |
| 4,617,933 | 10/1986 | Hasson ......................... 128/348 |
| 4,645,492 | 2/1987 | Weeks .......................... 604/174 |
| 4,653,475 | 3/1987 | Seike et al. ..................... 128/4 |
| 4,675,006 | 6/1987 | Hrushesky ................... 604/180 |
| 4,699,616 | 10/1987 | Nowak et al. ................ 604/180 |
| 4,717,385 | 1/1988 | Cameron et al. ............. 604/174 |
| 4,755,173 | 7/1988 | Konopka et al. ............. 604/167 |
| 4,767,411 | 8/1988 | Edmunds ..................... 604/180 |
| 4,787,892 | 11/1988 | Rosenberg .................... 604/170 |
| 4,808,162 | 2/1989 | Oliver ............................ 604/180 |
| 4,838,867 | 6/1989 | Kalt et al. ..................... 604/180 |
| 4,856,504 | 8/1989 | Yamamoto et al. ........... 604/180 |
| 4,874,380 | 10/1989 | Hesketh ....................... 604/180 |
| 4,875,259 | 10/1989 | Appeldorn ..................... 24/576 |
| 4,883,053 | 11/1989 | Simon ......................... 128/303 B |

(List continued on next page.)

FOREIGN PATENT DOCUMENTS 0487175 5/1992 European Pat. Off. .

OTHER PUBLICATIONS

Leaflet of product information entitled "Reclosable Fasteners" by 3M, No. 70-0704-8739-5, Apr. 1991.
Leaflet of product information entitled "Scotchmate ™ Hook and Loop Fasteners" by 3M, No. 70-07-01-0819-9(312)ii, Oct. 1989.
Leaflet of product information entitled "Dual Lock ™ Reclosable Fasteners", by 3M, No. 70-0702-02-77-8(1021.5)R.
Leaflet of product information entitled "Dual Lock ™ Reclosable Fasteners", by 3M, No. 70-0703-75-34-3(222)R1, Jan. 1992.
Leaflet of product information entitled "Scotchmate ™ Hook and Loop Fasteners", by 3M, No. 70-0702-6372-1(101)R1, Jan. 1990.
"The Surgical Armamentarium", Instruments Professional Equipment, by American V. Mueller (Division of American Hospital Supply Corporation), p. 202, No. TS26172CS, 1980.

*Primary Examiner*—John D. Yasko
*Assistant Examiner*—Frank Wilkens, III
*Attorney, Agent, or Firm*—Gary L. Griswold; Walter N. Kirn; Jeffrey J. Hohenshell

[57] ABSTRACT

An anchor sheet and anchor body for holding a cannula within the abdominal cavity of a patient is described. The cannula is used during a laparoscopic surgical procedure. The anchor sheet and anchor body assist in holding the cannula in a preferred orientation relative to the abdominal cavity. An attachment mechanism such as a hook and loop fastener may be utilized to connect the anchor sheet to the anchor body.

32 Claims, 3 Drawing Sheets

U.S. PATENT DOCUMENTS

| | | | |
|---|---|---|---|
| 4,915,694 | 4/1990 | Yamamoto et al. | 604/180 |
| 4,921,479 | 5/1990 | Grayzel | 604/53 |
| 4,932,943 | 6/1990 | Nowak. | |
| 4,952,618 | 8/1990 | Olsen | 524/17 |
| 4,959,265 | 9/1990 | Wood et al. | 428/343 |
| 4,985,019 | 1/1991 | Michelson | 604/180 |
| 4,986,815 | 1/1991 | Schneider | 604/180 |
| 5,009,642 | 4/1991 | Sahi | 604/158 |
| 5,009,643 | 4/1991 | Reich et al. | 604/165 |
| 5,026,352 | 6/1991 | Anderson | 604/178 |
| 5,069,206 | 12/1991 | Crosbie | 128/207.17 |
| 5,073,169 | 12/1991 | Raiken | 604/174 |
| 5,077,870 | 1/1992 | Melbye et al. | 24/452 |
| 5,098,399 | 3/1992 | Tollini | 604/180 |
| 5,100,393 | 3/1992 | Johnson | 604/180 |
| 5,105,807 | 4/1992 | Kahn et al. | 128/DIG. 26 |
| 5,112,310 | 5/1992 | Grobe | 604/175 |
| 5,112,321 | 5/1992 | Hiltebrandt | 604/264 |
| 5,122,122 | 6/1992 | Allgood | 604/174 |
| 5,137,520 | 8/1992 | Maxson et al. | 604/180 |
| 5,147,316 | 9/1992 | Castillenti | 604/164 |
| 5,158,553 | 10/1992 | Berry et al. | 604/248 |
| 5,160,323 | 11/1992 | Andrew | 604/158 |
| 5,176,648 | 1/1993 | Holmes et al. | 604/164 |
| 5,176,649 | 1/1993 | Wakabayashi | 604/164 |
| 5,176,652 | 1/1993 | Littrell | 604/167 |
| 5,176,697 | 1/1993 | Hasson et al. | 606/191 |
| 5,183,471 | 2/1993 | Wilk | 604/284 |
| 5,186,712 | 2/1993 | Kelso et al. | 604/177 |
| 5,196,266 | 3/1993 | Lu et al. | 428/355 |
| 5,201,101 | 4/1993 | Rouser et al. | 24/575 |
| 5,201,714 | 4/1993 | Gentelia et al. | 604/167 |
| 5,203,773 | 4/1993 | Green | 604/104 |
| 5,207,652 | 5/1993 | Kay | 604/180 |
| 5,209,736 | 5/1993 | Stephens et al. | 604/164 |
| 5,211,633 | 5/1993 | Stouder, Jr. | 604/167 |
| 5,211,654 | 5/1993 | Kaltenbach | 606/191 |
| 5,215,531 | 6/1993 | Matson et al. | 604/180 |
| 5,217,441 | 6/1993 | Shichman | 604/283 |
| 5,217,451 | 6/1993 | Freitas | 606/1 |
| 5,221,264 | 6/1993 | Wilk et al. | 604/167 |
| 5,221,281 | 6/1993 | Klicek | 606/45 |
| 5,226,890 | 7/1993 | Ianniruberto et al. | 604/164 |
| 5,232,440 | 8/1993 | Wilk | 604/49 |
| 5,234,455 | 8/1993 | Mulhollan | 606/191 |
| 5,248,298 | 9/1993 | Bedi et al. | 604/51 |
| 5,248,302 | 9/1993 | Patrick et al. | 604/178 |
| 5,257,973 | 11/1993 | Villasuso | 604/49 |
| 5,257,975 | 11/1993 | Foshee | 604/105 |
| 5,263,939 | 11/1993 | Wortrich | 604/174 |

CANNULA ANCHOR

TECHNICAL FIELD

The present invention is directed to a trocar cannula anchor for holding the cannula within the abdominal cavity of a patient use during a laparoscopic surgical procedure.

BACKGROUND

A large number of abdominal surgical procedures are performed with laparoscopic techniques in order to avoid a large skin incision. Typically in laparoscopic surgery, a special needle (e.g. a needle similar to the needles described in U.S. Pat. No. 4,808,168 and U.S. patent application Ser. No. 07/808,152) is inserted through the skin, and used to pressurize the abdominal cavity with an insufflating gas such as carbon dioxide ($CO_2$). Once the abdomen is adequately dilated, the needle is removed and a rigid access tube or cannula with a diameter larger than the pneumoneedle (for example 5, 10 or 11 mm) is passed through the skin in generally the same location.

The cannula provides access for laparoscopic surgical tools or instruments such as a laparoscope, a stapler or a surgical clip applier. Examples of such surgical instruments are described in U.S. Pat. Nos. 5,040,715, 5,084,057, 5,100,420, 5,171,247, 5,171,249 and 5,176,695. To drive the access tube through the skin, the surgeon places a trocar in the lumen of the cannula to provide a sharp, leading edge for cutting tissue.

The art is replete with trocar and cannula assemblies, including those shown in U.S. Pat. Nos. 4,535,773, 4,601,710, 4,654,030, 4,902,280, 4,931,042, 5,104,382, 5,116,353 and 5,152,754. Existing trocar and cannula assemblies encounter problems because, after the cannula has been inserted into the abdominal cavity, the cannula tends to become displaced from the abdominal cavity (e.g. the cannula tends to become dislodged from the abdominal cavity) due to a variety of factors. Those factors include friction between the laparoscopic tool and the inner surfaces of the cannula which tend to provide a removal force on the cannula when the laparoscopic tool is removed from the abdominal cavity (and cannula), and the frequent manipulation of laparoscopic instruments such as clip appliers and staplers within the cannula by the surgeon. Even an inadvertent jar of the cannula by medical personnel may dislodge the cannula from the abdominal cavity.

Obstacles associated with the surgical environment complicate the task for devices which are intended to retain the cannula within the abdominal cavity. The obstacles include friction reducing agents such as fluids and fat tissue which deleteriously affect parts which rely on friction, and adhesive contaminants such as blood and other liquids which may deleteriously affect an adhesive bond with the skin of a patient.

The art has diverse devices for addressing this problem. For example, U.S. Pat. No. 5,009,643 to Reich et al. and European Patent Application No. 0 494 520 disclose a cannula having anchoring threads. The cannula is screwed into the tissue of the abdominal wall and the anchoring threads hold the cannula in the abdominal cavity. Other, similar approaches include locating a member at the distal end of the cannula which expands once the cannula is within the abdominal cavity. See for example, U.S. Pat. No. 5,147,316 to Castillenti (balloon), and U.S. Pat. No. 5,122,122 to Allgood (mushroom hinged member). However, some persons in the surgical field hold these approaches in low regard due to the belief that they may unduly traumatize tissue.

Other approaches to this problem are shown in U.S. Pat. No. 5,073,169 to Raiken and U.S. Pat. No. 5,137,520 to Maxson et al. Those patents disclose a device having a hole through which the cannula is threaded. Generally, the hole is sized to form a tight friction fit between the device and the cannula. The device is also adhesively adhered to the skin of a patient.

The Origin Trocar Gripper TM has been on sale in this country by Origin Medsystems, Inc. prior to the filing date of the present application. The Origin Trocar Gripper TM comprises a generally flat patch with an aperture through which the cannula is threaded. The aperture is sized for a friction fit between the cannula and the patch. The friction fit assists in holding the cannula within the abdominal cavity. However, the friction reducing agents mentioned above may adversely affect the performance of this device.

BRIEF DESCRIPTION OF THE INVENTION

According to the present invention there is provided an anchor sheet and anchor body for use in a laparoscopic surgical procedure to hold a cannula within the abdominal cavity of a patient. The anchor sheet and body provide a device which (1) firmly retains or holds a cannula within the abdominal cavity of a patient during a laparoscopic surgical procedure despite the presence of materials in the surgical environment which may deleteriously affect elements which rely on an adhesive or frictional engagement, (2) may optionally releasably, repositionably and reusably hold the cannula in a plurality of positions relative to the abdominal cavity during a laparoscopic surgical procedure, (3) optionally may be installed even after the cannula has been inserted into the abdominal cavity of a patient, (4) is believed to reduce the trauma to the skin of a patient should the cannula be inadvertently removed from the abdominal cavity without first removing the anchor sheet, and (5) is believed to restrict the amount of a particular type of tissue trauma relative to a threaded type anchor.

In particular, the anchor body provides a device which (1) includes an easily adjustable lever which serves as an indicator to inform a user whether the anchor body is firmly attached to the cannula, (2) is conveniently and efficiently attached to the cannula with little effort from a user, and (3) may limit the depth of insertion of the cannula into the abdominal cavity to avoid an undue depth of penetration of the cannula should, for example, the cannula be inadvertently bumped during the laparoscopic surgical procedure. If the anchor body is applied prior to insertion of the cannula and trocar assembly into the abdominal cavity, the anchor body may serve to limit the amount of insertion of the cannula and its attendant trocar with sharp cutting surfaces. Thus, the anchor body may serve to keep the sharp trocar cutting surfaces spaced from sensitive internal tissues such as internal organs.

According to the present invention, there is provided an anchor body including a sleeve portion having proximal and distal surfaces, a through passage for receiving the cannula, and a means, such as a locking cam, for mounting the anchor body to the cannula. The locking cam is mounted for movement relative to the sleeve portion between a release position which affords relative movement between the sleeve portion and cannula while the cannula is within the through passage, and a locking position in which movement of the sleeve portion relative to the cannula is restricted and in which the cannula is firmly attached to the anchor body.

Preferably, the anchor body also has a flexible, friction collar between the locking cam and the cannula that is clamped between the locking cam and the cannula when the cannula is within the through passage and the locking cam is in the locking position. The friction collar is adapted to constrict about the cannula to firmly hold the cannula relative to the anchor body. The locking cam may comprise a lever and an eccentric cam surface.

In a first embodiment of the anchor body, the sleeve portion comprises first and second portions, and the anchor body has an opening means, such as a hinge, that mounts the first and second portions for relative pivotal movement between an open position in which the cannula may be placed within the through passage, and a closed position. In another embodiment of the anchor body, the sleeve portion is an integral, monolithic element.

In the first embodiment of anchor body, the sleeve portion comprises securing means, such as an arm with a detent on one of the first and second portions and a cooperable groove on the other of the first and second portions for releasably securing the first and second portions in the closed position.

The present invention may also be described as an anchor sheet for use with the anchor body. According to the present invention, there is provided an anchor sheet comprising first and second major side surfaces and a hole which affords passage of the cannula. The second major side surface has an adhesive for removably adhering the sheet to the skin of the patient.

The present invention may alternatively be described as an attachment means, associated with either the first major side surface of the anchor sheet or the distal surface of the anchor body or both. The attachment means attaches the first major side surface of the sheet to the distal surface of the anchor body.

Preferably, the attachment means is a releasable and reusable attachment means that affords attachment of the anchor sheet to the distal surface of the anchor body, a subsequent release in which the distal surface of the anchor body is spaced from the anchor sheet, and then a subsequent attachment of the sheet to the distal surface of the anchor body. Also preferably, the attachment means comprises a fastener which is free of an adhesive that may attract dust and other contaminants to the surgical site.

The relative shapes of the distal end surface of the anchor body and the first major side surface of the anchor sheet afford positioning of the cannula in a plurality of orientations relative to the abdominal cavity. Preferably, the first major side surface of the sheet is planar and the distal surface of the sleeve portion comprises a convex surface.

BRIEF DESCRIPTION OF THE DRAWINGS

The present invention will be further described with reference to the accompanying drawing wherein like reference numerals refer to like parts in the several views, and wherein.

DETAILED DESCRIPTION

Figure 1:
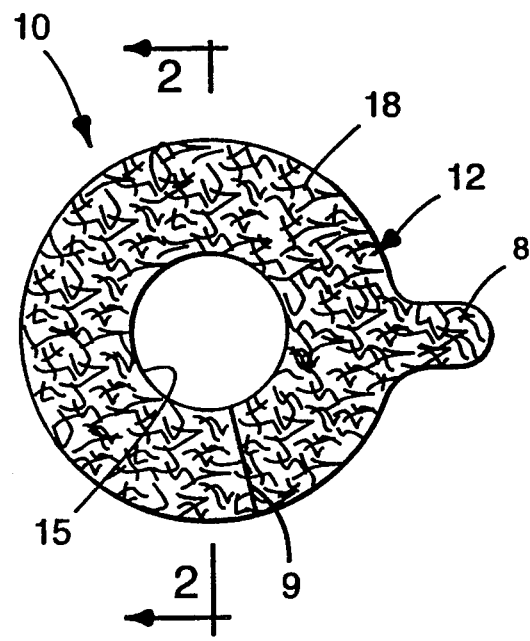
FIG. 1 is a top view of an anchor sheet according to the present invention.

Referring now to FIGS. 1 through 6 of the drawing there is shown an example of an anchor sheet generally designated by reference character 10 and an anchor body generally designated by reference character 20 according to the present invention.

The anchor sheet 10 and body 20 are designed for use with a cannula 1 used during laparoscopic surgery. Typically, the cannula 1 is inserted through the abdominal wall 2 of a patient and into the patient's abdominal cavity 3 by using a trocar which is well known in the art. The anchor body 20 and sheet 10 cooperate to hold the cannula 1 within the abdominal cavity 3 even when surgical instruments such as laparoscopes, staplers or clip appliers are manipulated by a surgeon within the cannula 1.

The anchor body 20 is preferably releasably attached to the cannula 1, but may be integrally molded therewith (not shown). The anchor body 20 comprises a sleeve portion 22 having proximal 23 and distal 24 end surfaces, and surfaces defining a through passage 25 which open onto the proximal 23 and distal 24 end surfaces. The through passage 25 receives the cannula 1.

The through passage 25 has proximal and distal ends. Preferably, in the embodiment of anchor body 20 shown in FIGS. 3 through 6, the sleeve portion 22 comprises first 26 and second 27 portions, and opening means such as a hinge 30 for pivotably mounting the first 26 and second 27 portions.

Figure 3:
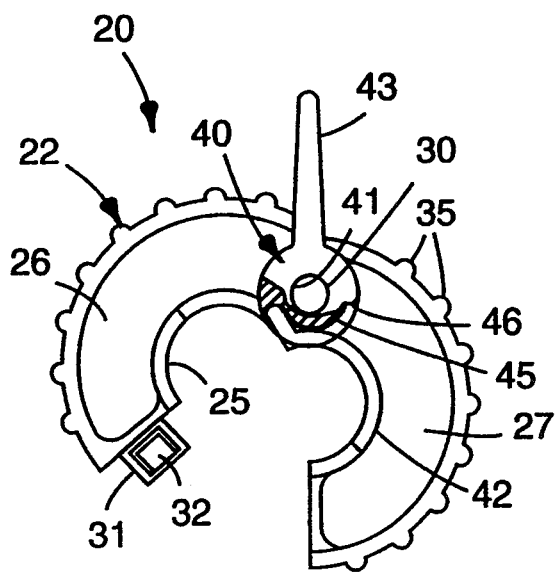
FIG. 3 is a top view of a first embodiment of anchor body according to the present invention illustrating first and second portions of a sleeve portion in an open position, and illustrating a locking cam in a release position.
Figure 4:
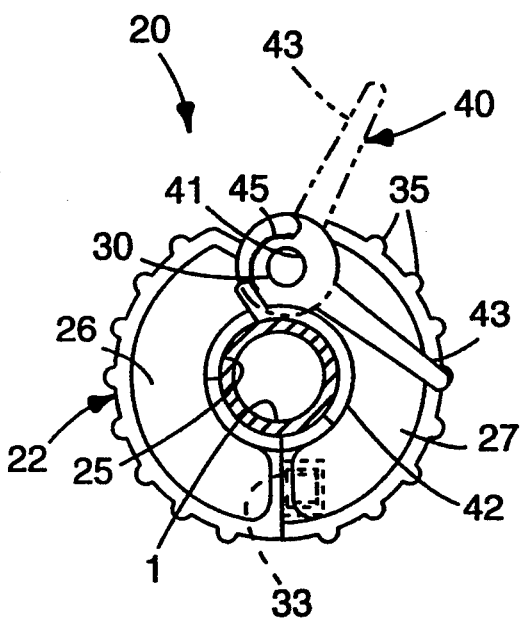
FIG. 4 is a top view of the first embodiment of anchor body according to the present invention which shows the first and second portions of the sleeve portion in a closed position about a sectioned cannula and which shows the locking cam in a locking position with solid lines and in a release position with dashed lines.
Figure 5:
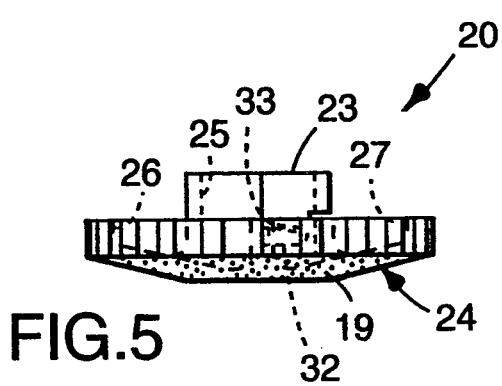
FIG. 5 is a side view of the anchor body of FIG. 4 with the cannula omitted.

The hinge 30 mounts the first 26 and second 27 portions for movement between (1) an open position (FIG. 3) in which the cannula 1 may be received within the through passage 25 without requiring the cannula 1 to be threaded through the proximal or distal ends of the through passage 25, and (2) a closed position (FIG. 4) in which portions of the first 26 and second 27 are more closely spaced than in the open position (Compare FIGS. 3 and 4). The hinge 30 allows the anchor body 20 to be placed on a cannula 1 from the side of the cannula 1 rather than from an end. Thus, the anchor body 20 may be placed on the cannula 1 even after the cannula 1 has been inserted in the abdominal cavity 3 so that the cannula 1 need not be withdrawn merely to place the anchor body 20 on the cannula 1. This feature is particularly advantageous for surgeons who wish to avoid using a cannula anchor unless absolutely necessary or for surgeons who do not realize that a cannula anchor will be required (e.g. the cannula may slip relative to the abdominal wall more than expected during a surgical procedure).

Preferably the hinge 30 comprises a pin on the first portion 26 that is adapted to be received in a through hole in the second portion 27. The pin and through hole are sized for a friction fit but allow the user to easily manually move the first and second portions 26 and 27 between the open and closed positions. It is appreciated that the positions of the pin and through hole on the first and second portions 26 and 27 may be reversed.

In the preferred embodiment of the anchor body 20, the sleeve portion 22 also has a securing means for releasably securing the first 26 and second 27 portions in the closed position. For example, the securing means may comprise the first sleeve portion 26 having an arm 31 with a detent 32, and a groove 33 on the second sleeve portion 27 for receiving the detent 32 of the arm 31. The detent 32 provides a snap fit into the groove 33 to releasably secure the first 26 and second 27 portions in the closed position.

The sleeve portion 22 has peripheral surfaces between the proximal 23 and distal 24 end surfaces. Preferably the peripheral surfaces include a plurality of grasping ribs 35 for enhancing a user's grip on the sleeve portion 22.

The anchor body 20 also includes a means for attaching the anchor body to the cannula 1 that is preferably a releasable means. The means for attachment the anchor body 20 to the cannula 1 comprises a locking cam 40, and preferably a friction collar 42 situated between the locking cam 40 and the cannula 1 when the cannula 1 is within the surfaces defining the through passage 25.

The locking cam 40 is mounted for movement relative to the sleeve portion 22 between a release position (FIG. 4, dashed lines) which affords relative movement between the sleeve portion 22 and the cannula 1 within the through passage 25, and a locking position (FIG. 4, solid lines) with the friction collar 42 clamped between the locking cam 40 and the cannula 1 when the cannula 1 is within the through passage 25 to restrict movement of the sleeve portion 22 relative to the cannula 1 and to firmly attach the cannula 1 to the anchor body 20.

Preferably the locking cam 40 is pivotably mounted on the sleeve portion 22 by having a hole 41 that receives the same pin (described above) which is used to form a portion of the hinge 30 that allows the first and second portions 26 and 27 to move from the open to the closed positions.

Also preferably, the locking cam 40 comprises a lever 43 adapted to be manipulated by a user's digits. A user, such as a surgeon, may conveniently manipulate the locking cam 40 with one hand. Unlike prior art clamps which require two hands to operate, the lever 43 allows the locking cam 43 to be manipulated between the release and locking positions with only one hand. This frees the surgeon's other hand for other tasks during the laparoscopic procedure. A rib on the end of the friction collar 42 is provided to abut a stop surface on the locking cam 40 to prevent over pivoting of the lever 43, and to define the release position (see FIG. 4).

When the lever 43 is in the position shown in FIG. 4 by dashed lines, it indicates that the locking cam 40 is in the release position, and when the lever 43 is in the position shown in FIG. 4 by solid lines, it indicates that the locking cam 40 is in the locking position. This allows a user to quickly reference whether the anchor body 20 is firmly clamped to the cannula 1 which may not be possible with some prior art radial clamps or collets.

The locking cam 40 also preferably comprises an eccentric cam surface 45 with a locking portion 46. The locking cam 40 is operatively associated with the cannula 1 and clamps the friction collar 42 therebetween when the locking cam 43 is in the locking position. In the locking position, the friction collar 42 is firmly clamped between the locking portion 46 of the eccentric cam surface 45 and the cannula 1.

Alternatively, but not preferably, the friction collar 42 may be omitted from the anchor body 20. In this embodiment, the eccentric cam surface 45 and locking portion 46 of the locking cam 40 would directly engage the cannula 1 when the cannula 1 is within the through passage 25 and the locking cam 40 is moved to the closed position.

Preferably, the friction collar 42 is constructed from a flexible material that constricts about the cannula 1 to form a tight friction fit when the locking cam 40 is moved to the locking position. Any suitable materials may be utilized as the material for the friction collar 42. For example, acrylobutadiene-styrene (ABS) plastic, polyvinyl chloride (PVC), polycarbonate, or polypropylene are all materials which are believed suitable for use as the friction collar 42.

When the anchor body 20 is attached to the cannula 1, the anchor body 20 limits the amount of insertion of the cannula 1 into the abdominal cavity 3 to avoid an undue depth of penetration of the cannula 1. Although it is not recommended as a positive safety feature, if the anchor body 20 is attached to the cannula 1 prior the insertion of the cannula 1 into the body cavity 3, the anchor body 20 may serve to reduce the chances of accidental over insertion of the cannula 1 (and especially the sharp trocar tip used to insert the cannula) into the abdominal cavity 3. An undue depth of insertion into the abdominal cavity 3 may result in damage to sensitive tissue, particularly underlying organs.

In an alternative, but not preferred embodiment of the present invention, the distal end surface 24 of the anchor body 20 may comprise a substantially flat (not shown) or substantially concave (not shown) surface with an adhesive adhered thereto that affords adhesive attachment of the anchor body 20 directly to the skin of a patient. The adhesive may comprise any of the medical grade adhesives discussed below in conjunction with the anchor sheet 10. Thus, optionally, but not preferably, the anchor body 20 may be used independent of the use of the anchor sheet 10.

In the preferred embodiment of the present invention, the anchor body 20 is used in conjunction with the anchor sheet 10 to hold the cannula 1 within the abdominal cavity 3 of a patient. In this embodiment, the distal end surfaces 24 of the sleeve portion 22 comprise a convex, substantially curved surface (see FIGS. 5 and 6).

Figure 2:
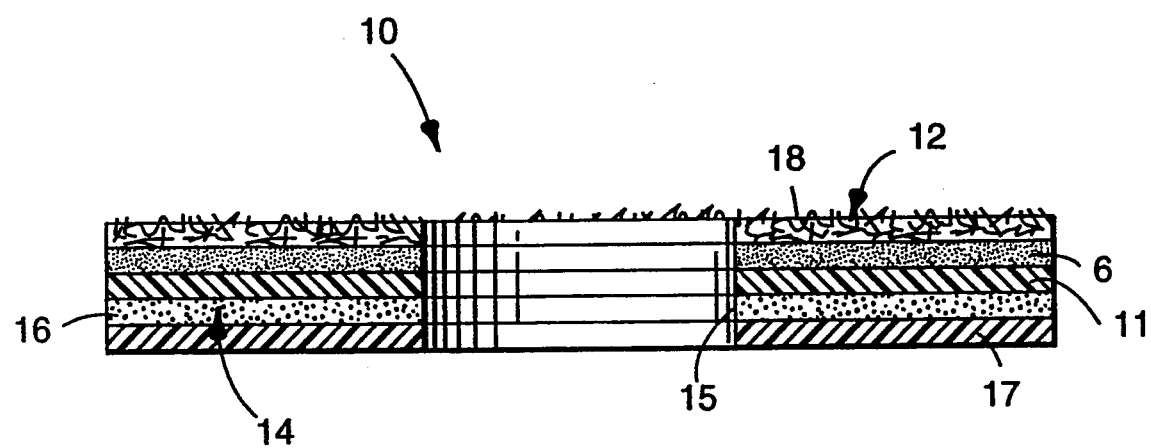
FIG. 2 is an enlarged sectional view of the anchor sheet of FIG. 1 taken approximately along lines 2—2 of FIG. 1.

Referring now to FIGS. 1 and 2, there is shown the anchor sheet 10 also according to the present invention.

The anchor sheet 10 comprises first 12 and second 14 major side surfaces, and surfaces 15 defining a hole extending between the first 12 and second 14 major side surfaces which afford passage of the cannula 1.

As shown in FIG. 1, the sheet 10 is preferably annulus or annular shaped to provide a beneficial resistance to edge lift. The sheet 10 also preferably includes a slit 9 extending from the hole 15 to the outer periphery of the sheet 10. The slit 9 allows the sheet 10 to be adhered to the skin and about the cannula 1 even after the cannula 1 has been placed in the abdominal cavity 3 of a patient. Thus, the cannula 1 need not be threaded through the hole 15.

Figure 6:
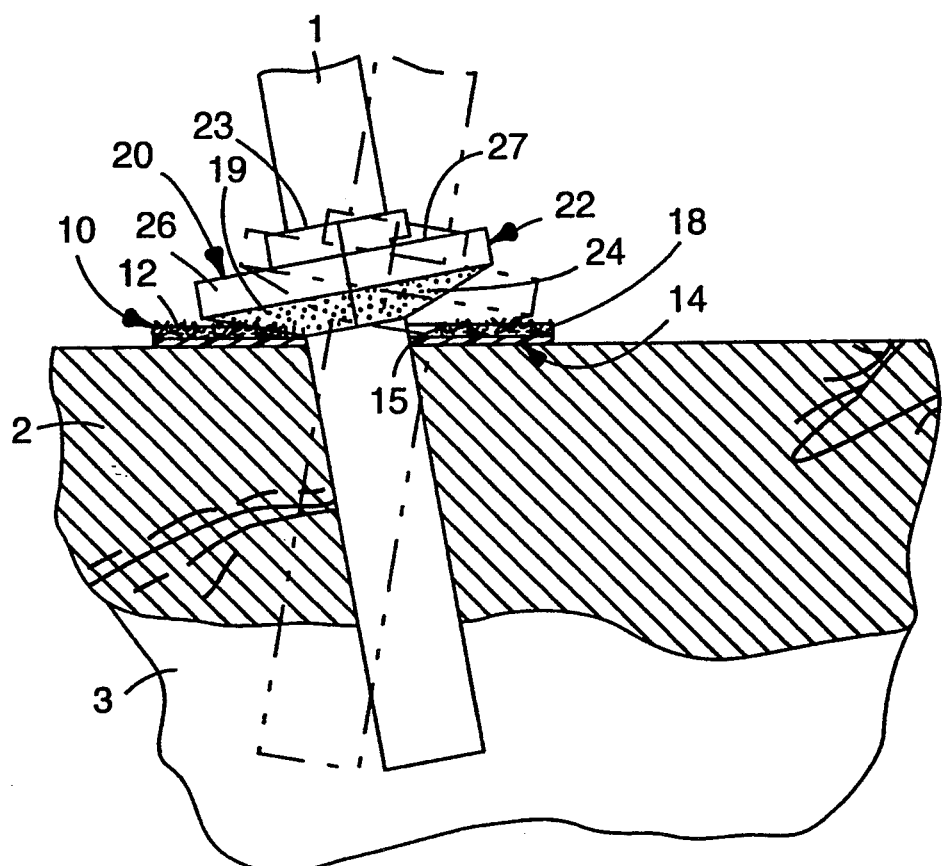
FIG. 6 is a side view of the anchor body and sheet according to the present invention which shows the sheet attached to the skin of a patient and the anchor body attached to a cannula that is inserted into the abdominal cavity of a patient, and which also shows the anchor sheet and body holding the cannula in first (solid lines) and second (dashed lines) orientations relative to the abdominal cavity.

The surfaces defining the hole 15 should be generally circular to cooperate with the generally circular cross-section of the cannula 1. As shown in FIG. 6, the hole 15 may have a diameter that is larger than the diameter of the cannula 1 so that the cannula may be manipulated relative to the sheet 10.

When the diameter of the hole 15 is larger than the diameter of the cannula 1, the cannula 1 is substantially free of contact with the sheet 10 and the adhesive 16 (described in greater detail below) so that the cannula 1 may be freely manipulated relative to the sheet 10. Additionally, when the diameter of the hole 15 is larger the diameter of the cannula 1, the risks of adhesive 16 transfer from the sheet 10 to the cannula 1 are attenuated.

Alternatively, the surfaces defining the hole 15 may be sized and shaped to afford a friction fit between the anchor sheet 10 and the cannula 1. Such a friction fit affords resistance to fluid ingress to the operative site, and insufflatory gas egress from the operative site.

Preferably, the anchor sheet 10 comprises a backing 11 that is flexible and conformable to the irregular anatomical surface topography, even when the surface is flexed. Representative backing materials include nonwoven fibrous webs, fibrous film webs, knits, and other backing materials such as resilient, flexible fine-celled thermoplastic foams. A preferred backing material is a polymeric film.

The backing 11 is preferably a high moisture vapor permeable but liquid-barrier film of, for example, porous polyethylene such as disclosed in U.S. Pat. No. 4,539,256 to Shipman, or polyurethane moisture vapor permeable films such as that disclosed in U.S. Pat. No. 4,598,004 to Heinecke. For example, the backing 11 may have a thickness of about 0.128 to about 0.768 millimeters, and more preferably about 0.256 millimeters.

The second major side surface 14 has an adhesive 16 generally permanently adhered thereto for removably adhering the sheet 10 to the skin of the patient. The adhesive 16 preferably comprise a "medical grade" adhesive or any adhesive which is suitable for contact with the skin of a patient and sufficiently strong to hold or immobilize the sheet 10 to the skin. The adhesive 16 should be able to at least temporarily withstand the deleterious effects of contaminants such as blood and fat tissue encountered during the surgical environment. Although not required, the adhesive 16 could perform a sealing function to resist fluid ingress to the operative site, and insufflatory gas egress from the operative site. Additionally, the adhesive 16 is preferably moisture vapor permeable to avoid significantly detracting from the moisture vapor permeability of the backing 11.

As an example, not intended to be limiting, the biocompatible, hypo-allergenic, copolymer acrylate pressure sensitive adhesives described in U.S. Pat. No. 4,598,004 to Heinicke (herein incorporated by reference) may be utilized as the adhesive. The polyvinyl ether adhesives described therein may also be used. Also, a suitably strong adhesive made in accordance with the teachings of U.S. Pat. No. 4,952,618 to Olsen (herein incorporated by reference) may also be utilized as the adhesive 16. The adhesive 16 may be about 0.025 millimeters to about 0.075 millimeters thick.

As shown in FIG. 2, a removable, peel-off release liner 17 may be present to protect the adhesive 16 until just prior to use of the sheet 10, when it can be peeled off by a user. Examples of liners suitable for use with the sheet 10 include coated liners made from kraft papers, polyethylene, polypropylene or polyester. The liners may be coated with releasing agents such as fluorochemicals or silicones. The preferred liners are silicone coated release papers, polyolefin or polyester films.

The anchor sheet 10 also includes an attachment means, associated with the first major side surface 12, for attaching the sheet 10 to the distal surface 24 of the anchor body 20 to hold the cannula 1 within the abdominal cavity 3. As used herein, the phrase "attachment means" should be construed broadly to include structures which function to attach the sheet 10 to the distal surface 24 of the anchor body 20 to hold the cannula 1 within the abdominal cavity 3. The attachment means may be present on only the first major side surface 12 of the sheet 10 or only the distal surface 24 of the body 20. Preferably, both the first major side surface 12 of the sheet 10 and the distal surface 24 of the body 20 have a portion of the attachment means.

Figure 9:
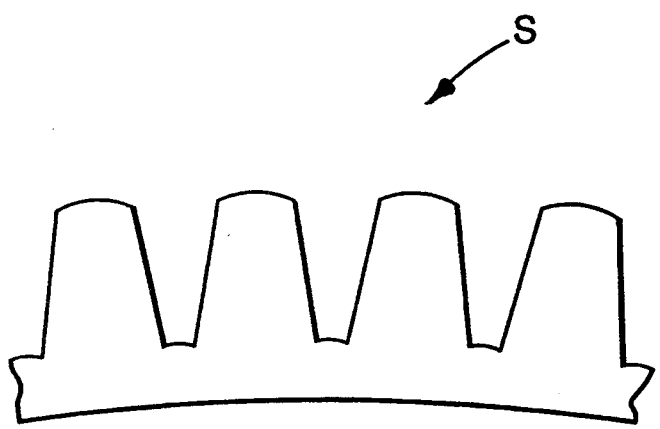
FIG. 9 is a side view of an alternative attachment means.

Particular examples, not intended to be limiting, which are believed to be able to function as the attachment means include one or combinations of: (1) The distal surface 24 of the anchor body 20 or the first major side surface 12 of the sheet 10 may have a pressure sensitive adhesive for adhering the body 20 to the sheet 10. The adhesive need not be a "medical grade" or hypo-allergenic adhesive. For example, the adhesive may comprise a suitably aggressive repositionable, pressure sensitive adhesive made in accordance with the teachings of U.S. Pat. No. 3,691,140 to Silver or U.S. Pat. No. 4,994,322 to Delgado et al. the entire contents of each of which are herein expressly incorporated by reference. (2) Each of the distal end surface 24 and the first major side surface 12 may comprise a structured surface having a plurality of tapered elements as taught in U.S. Pat. No. 4,875,259 to Appeldorn or U.S. Pat. No. 5,201,101 to Rouser et al. the entire contents of each of which are herein expressly incorporated by reference. FIG. 9 illustrates a structured surface S adapted to be placed on an arcuate surface. (3) In a preferred embodiment of attachment means, the distal end surface 24 of the anchor body 20 and the first major side surface 12 may be attached by a hook and loop type fastener. The art is replete with hook and loop type fasteners, such as the fasteners described in U.S. Pat. Nos. 3,359,980 to Rosenblatt, 3,694,867 to Stumpf, 3,913,183 to Brumlik, 4,169,303 to Lemelson, 4,609,581 to Ott, 4,739,635 to Conley et al., 4,761,318 to Ott et al. and 4,770,917 to Tochacek et al., the entire contents of each of which is herein expressly incorporated by reference. Commercial sources for hook and loop type fasteners include Velcro USA of Manchester N.H., and the Scotchmate TM brand hook and loop fasteners generally available from the Minnesota Mining and Manufacturing Co. (3M) of St. Paul, Minn. (4) It is also believed that the fasteners described in U.S. Pat. Nos.

3,192,589 to Pearson, 3,353,663 to Kayser et al., 3,408,705 to Kayser et al., 4,959,265 to Wood et al., 5,077,870 to Melbye et al., and 5,196,266 to Lu et al., and EPO published application no. 382 420 to Lu et al. may also be used as the attachment means of the present invention. A commercial example of one such fastener is the Dual Lock ™ reclosable fasteners generally available from the Minnesota Mining and Manufacturing Co. (3M) of St. Paul, Minn. (5) Even a plurality of stud and eyelet fasteners strategically located on the anchor body and sheet may function as an attachment means for the present invention.

Preferably, the attachment means comprises a releasable and reusable attachment means that affords attachment of the sheet 10 to the distal surface 24 of the anchor body 20, a subsequent release in which the distal surface 24 of the anchor body 20 is spaced from the sheet 10, and then a subsequent attachment of the sheet 10 to the distal surface 24 of the anchor body 20. Such a feature facilitates repositioning of the cannula 1 in relation to the abdominal cavity 3 and is described in greater detail below.

FIGS. 1, 2 and 6 illustrate a preferred embodiment of attachment means according to the present invention. As shown in FIG. 1, the first major side surface 12 of the sheet 10 preferably comprises a hook portion 18 and the distal end surface 24 of the anchor body 20 includes a loop portion 19 of a hook and loop type fastener. Alternatively the distal end surface 24 may comprise the hook portion and the first major side surface 12 may comprise the loop portion.

FIG. 2 illustrates one manner of forming the first major side surface 12. A sheet or film having the hook portion 18 on one side and an adhesive 6 on the opposite side is adhesively adhered to the backing 11 by the adhesive 6. The adhesive 6 should be more aggressive than the adhesive 16 but need not be a medical grade adhesive.

The hook and loop fastener is a attachment means which is free of an adhesive. It is appreciated that adhesives may be contaminated by material such as dust that may adversely affect sanitary conditions during the surgical procedure. Also, the hook and loop fastener allows the anchor body 20 and cannula 1 to be suddenly removed from contact with the sheet 10 (and the cannula 1 from the abdominal cavity 3) should the need arise without requiring the user to remove the sheet 10 as well which could traumatize tissue.

The sheet 10 has a grasping finger or tab 8 that may be grasped by a user and pulled to peel the sheet 10 from adhesive attachment to the skin. The undersurface of the grasping finger 8 is free of adhesive to afford easy grasping of the finger 8 when the sheet 10 is adhered to the skin of a patient.

When a hook and loop type fastener is used as the attachment means, and when the first major side surface 12 of the sheet 10 and the distal end surface 24 of the anchor body are not mirror images of each other (in other words they are dissimilarly shaped), it is believed that the attachment means may assist in holding the anchor body 20 and cannula 1 in a plurality of orientations relative to the abdominal cavity 3.

Note FIG. 6 which shows the substantially flat surface 12 of sheet 10, and the substantially convex shape of the distal end surface 24 of the anchor body 20. The anchor body 20 and anchor sheet 10 may assist in holding the cannula in a first orientation relative to the abdominal cavity 3 (FIG. 6 solid lines), and the same anchor body 20 and sheet 10 may also hold the cannula 1 in a second orientation relative to the abdominal cavity 3 (FIG. 6 dashed lines) which may be helpful for some surgeons during a laparoscopic procedure. Thus, a hook and loop type fastener assists a surgeon in orienting the cannula in a desired orientation relative the abdominal cavity 3.

Preferably, the attachment means is designed such that the force required the separate the anchor body 20 from the anchor sheet 10 is less than the force required to separate the sheet 10 from the skin of a patient. Such a balancing of the strength of the attachment means with the strength of the adhesive 16 will facilitate the orientation of the cannula 1 in a plurality of positions relative the abdominal cavity 3, as a surgeon merely needs to pull the body 20 from the sheet 10 and reattach a different portion of the distal end surface 24 to the first major side surface 12 to provide a different orientation of the cannula 1 relative to the abdominal cavity.

Any suitable materials may be used to construct the sleeve 22 and locking cam 40. Acrylobutadiene-styrene (ABS) plastic, polyvinyl chloride (PVC), polycarbonate, or polypropylene are all materials which are suitable for use as the sleeve 22 and locking cam 40. The elements of the anchor body 20 may be constructed from a single, identical, unitary material or diverse materials could be utilized to construct each element.

Figure 7:
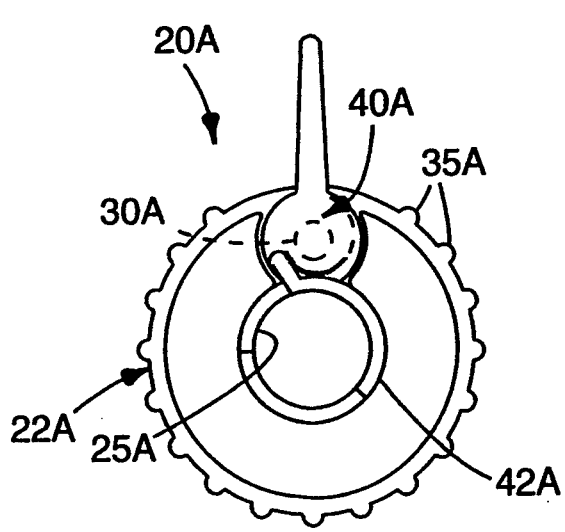
FIG. 7 is a top view of a second embodiment of anchor body according to the present invention.
Figure 8:
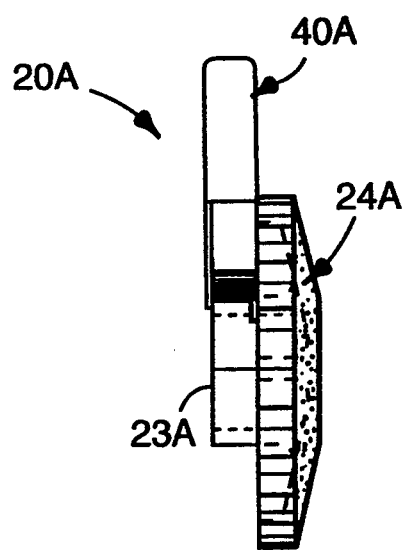
FIG. 8 is a side view of the anchor body of FIG. 7.

FIGS. 7 and 8 illustrate another embodiment of anchor body according to the present invention generally designated by reference character 20A. The anchor body 20A has many of the same elements as the anchor body 20 and are identified with the same reference character to which the suffix "A" has been added. Like the anchor body 20, the anchor body 20A has proximal 23A and distal 24A end surfaces, a through passage 25A, hinge 30A, grasping ribs 35A, locking cam 40A and an optional friction collar 42A. The distal end surface 24 may comprise any of the attachment means mentioned above. Unlike the sleeve portion 22, the sleeve portion 22A comprises a unitary, monolithic member which may be easier and less expensive to construct than the sleeve portion 22.

The present invention has now been described with reference to several embodiments thereof. It will be apparent to those skilled in the art that many changes or additions can be made in the embodiments described without departing from the scope of the present invention. For example, the hook portion 18 shown in FIG. 2 may be laminated to the backing 11 or the backing an hook portion 18 may comprise a single, monolithic piece. Thus, the scope of the present invention should not be limited to the structures described in this application, but only by structures described by the language of the claims and the equivalents of those structures.

What is claimed is:

1. An anchor sheet for use with a cannula that is adapted to be inserted within the abdominal cavity of a patient during a laparoscopic surgical procedure, the cannula having an anchor body attached thereto, the anchor body having a distal surface, the sheet comprising:
first and second major side surfaces and surfaces defining a hole extending between the first and second major side surfaces which afford passage of the cannula,
the second major side surface having an adhesive adhered thereto for removably adhering the sheet to the skin of the patient, and an attachment means, associated with the first major side surface, for attaching the sheet to the distal surface of the anchor body, wherein the attachment means is a releasable and reusable attachment means that affords attachment of the sheet to the distal surface of the anchor body, a subsequent release in which the distal surface of the anchor body is spaced from the sheet, and then a subsequent attachment of the sheet to the distal surface of the anchor body.

2. An anchor sheet according to claim 1 wherein the releasable and reusable attachment means and the distal surface of the anchor body comprise hook and loop fasteners.

3. An anchor sheet according to claim 1 wherein the releasable and reusable attachment means and the distal surface of the anchor body comprise structured surface fasteners.

4. An anchor sheet according to claim 1 wherein the cannula is generally cylindrical and has a diameter, and
the hole is generally circular and has a diameter that is larger than the diameter of the cannula.

5. An anchor sheet according to claim 1 wherein the sheet has a grasping finger that may be grasped by a user and pulled to peel the sheet from adhesive attachment to the skin, wherein the grasping finger is free of adhesive.

6. An anchor sheet according to claim 1 wherein the attachment means affords positioning of the cannula in a first position relative to the abdominal cavity and thereafter a second position relative to the abdominal cavity that is different than said first position.

7. An anchor sheet according to claim 1 wherein the sheet has a periphery, and
a slit extending from the periphery to the hole so that the sheet may be adhered to the skin and about the cannula even after the cannula is inserted in the abdominal cavity of a patient.

8. An anchor sheet according to claim 1 wherein the sheet comprises a flexible, conformable backing.

9. An anchor sheet for use with a cannula that is adapted to be inserted within the abdominal cavity of a patient during a laparoscopic surgical procedure, the cannula having an anchor body attached thereto, the anchor body having a distal surface,
the sheet comprising:
first and second major side surfaces and surfaces defining a hole extending between the first and second major side surfaces which afford passage of the cannula, the surfaces defining a hole affording a friction fit between the anchor sheet and the cannula,
the second major side surface having an adhesive adhered thereto for removably adhering the sheet to the skin of the patient, and
an attachment means, associated with the first major side surface, for attaching the sheet to the distal surface of the anchor body.

10. An anchor body for attachment to a cannula that is adapted to be inserted into the abdominal cavity of a patient during a laparoscopic surgical procedure,
the anchor body comprising:
a sleeve portion having proximal and distal surfaces, surfaces defining a through passage for receiving the cannula, said surfaces defining the through passage opening onto the proximal and distal surfaces,
a locking cam, and
means mounting the locking cam for movement relative to the sleeve portion between a release position which affords relative movement between the sleeve portion and cannula while the cannula is within the through passage, and a locking position in which movement of the sleeve portion relative to the cannula is restricted and in which the cannula is firmly attached to the anchor body,
wherein the anchor body is adapted to be used with an anchor sheet that is attached to the skin of a patient and which has a first major side surface opposite the skin of the patient, and
the anchor body comprises attachment means, associated with the distal surface, for attaching the anchor body to the first major side surface of the anchor sheet, wherein the attachment means is a releasable and reusable attachment means that affords attachment of the sheet to the distal surface of the anchor body, a subsequent release in which the distal surface of the anchor body is spaced from the sheet, and then a subsequent attachment of the sheet to the distal surface of the anchor body.

11. An anchor body according to claim 10 wherein the anchor body comprises a friction collar between the locking cam and the cannula when the cannula is within the surfaces defining the through passage, and
wherein, when the locking cam is in the locking position, the friction collar is clamped between the locking cam and the cannula when the cannula is within the through passage.

12. An anchor body according to claim 10 wherein the locking cam is pivotably mounted on the sleeve portion, and
the locking cam comprises a lever adapted to be manipulated by a user's digits, and adapted to indicate when the locking cam is in the locking position.

13. An anchor body according to claim 11 wherein the locking cam comprises an eccentric cam surface, operatively associated with the cannula, for clamping the friction collar therebetween when the locking cam is in the locking position.

14. An anchor body according to claim 10 wherein the sleeve portion has peripheral surfaces between the proximal and distal surfaces and the peripheral surfaces include a plurality of grasping ribs.

15. An anchor body according to claim 10 wherein the distal surface of the sleeve portion comprise a convex surface.

16. An anchor body according to claim 10 wherein the attachment means is free of an adhesive.

17. An anchor body according to claim 16 wherein the attachment means and the first major side surface of the anchor sheet comprise hook and loop fasteners.

18. An anchor body according to claim 16 wherein the attachment means and the first major side surface of the anchor sheet comprise a structured surface fastener.

19. An anchor body according to claim 10 wherein the attachment means affords positioning of the cannula in a first position relative to the abdominal cavity and a second position relative to the abdominal cavity that is different than said first position.

20. An anchor body according to claim 11 wherein the friction collar comprises a flexible material that is adapted to constrict about the cannula when the locking cam is in the locking position.

21. An anchor body according to claim 11 wherein, when the friction collar is clamped between the cannula and the locking cam in the locking position, the anchor body limits the amount of insertion of the cannula into the abdominal cavity to avoid an undue depth of penetration of the cannula.

22. An anchor body according to claim 10 wherein the sleeve portion comprises a unitary, monolithic member.

23. An anchor body for attachment to a cannula that is adapted to be inserted into the abdominal cavity of a patient during a laparoscopic surgical procedure,
the anchor body comprising:
a sleeve portion having proximal and distal surfaces,
surfaces defining a through passage for receiving the cannula, said surfaces defining the through passage opening onto the proximal and distal surfaces, wherein the through passage has proximal and distal ends;
the sleeve portion comprises first and second portions, and opening means mounting the first and second portions for movement between an open position in which the cannula may be placed within the through passage without being threaded through the proximal or distal ends of the through passage, and a closed position in which portions of the first and second portions are more closely spaced than in the open position,
a locking cam, and
means mounting the locking cam for movement relative to the sleeve portion between a release position which affords relative movement between the sleeve portion and cannula while the cannula is within the through passage, and a locking position in which movement of the sleeve portion relative to the cannula is restricted and in which the cannula is firmly attached to the anchor body.

24. An anchor body according to claim 23 wherein the opening means comprises a hinge for pivotably mounting the first and second portions.

25. An anchor body according to claim 23 wherein the sleeve portion comprises securing means for releasably securing the first and second portions in the closed position.

26. An anchor body according to claim 25 wherein the securing means comprises an arm having a detent on one of the first and second sleeve portions and a groove on the other of the first and second sleeve portions for receiving the detent of the arm to releasably secure the first and second portions in the closed position.

27. An anchor body for attachment to a cannula that is adapted to be inserted into a patient's abdominal cavity during a laparoscopic surgical procedure, and that is adapted for use with an anchor sheet having a first major side surface,
the anchor body comprising:
a sleeve portion having proximal and distal surfaces,
surfaces defining a through passage adapted to receive the cannula, the surfaces defining the through passage opening onto the proximal and distal surfaces,
means for attaching the sleeve portion to the cannula, and
an attachment means, associated with the distal surface, for attaching the anchor body to the first major side surface of the anchor sheet, wherein the attachment means is a releasably and reusable attachment means that affords orienting the cannula in a plurality of positions relative to the abdominal cavity.

28. An anchor according to claim 27 wherein the means for attaching the sleeve portion to the cannula comprises a locking cam, and the anchor body further comprises:
means mounting the locking cam for movement relative to the sleeve portion between a release position which affords relative movement between the sleeve portion and cannula while the cannula is within the through passage, and a locking position in which movement of the sleeve portion relative to the cannula is restricted and in which the cannula is firmly attached to the anchor body.

29. An anchor body according to claim 28 wherein the anchor body comprises a friction collar between the locking cam and the cannula when the cannula is within the surfaces defining the through passage, and
wherein, when the locking cam is in the locking position, the friction collar is clamped between the locking cam and the cannula when the cannula is within the through passage.

30. An anchor body for attachment to a cannula that is adapted to be inserted into a patient's abdominal cavity during a laparoscopic surgical procedure, and that is adapted for use with an anchor sheet having a first major side surface,
the anchor body comprising:
a sleeve portion having proximal and distal surfaces, the sleeve portion comprising first and second portions, surfaces defining a through passage adapted to receive the cannula, the surfaces defining the through passage opening onto the proximal and distal surfaces, wherein the through passage has proximal and distal ends;
means for attaching the sleeve portion to the cannula, and
an attachment means, associated with the distal surface, for attaching the anchor body to the first major side surface of the anchor sheet, and
opening means mounting the first and second portions for movement between an open position in which the cannula may be placed within the through passage without being threaded through the proximal or distal ends of the through passage, and a closed position in which portions of the first and second portions are more closely spaced than in the open position.

31. In combination, an anchor body and anchor sheet for holding a cannula within the abdominal cavity of a patient during a laparoscopic surgical procedure, the anchor body comprising:
a sleeve portion having proximal and distal surfaces;
the anchor sheet comprising:
first and second major side surfaces and surfaces defining a hole extending between the first and second major side surfaces which afford passage of the cannula,
the second major side surface having an adhesive adhered thereto for removably adhering the sheet to the skin of the patient; and
an attachment means, associated with the distal surface of the anchor body and the first major side surface of the anchor sheet, for attaching the anchor body to the first major side surface of the anchor sheet, wherein the attachment means is a releasable and reusable attachment means that affords attachment of the sheet to the distal surface of the anchor body, a subsequent release in which the distal surface of the anchor body is spaced from the sheet, and then a subsequent attachment of the sheet to the distal surface of the anchor body.

32. In combination, an anchor body and anchor sheet for holding a cannula within the abdominal cavity of a patient during a laparoscopic surgical procedure, the anchor body comprising:

a sleeve portion having proximal and distal surfaces; the anchor sheet comprising:

first and second major side surfaces and surfaces defining a hole extending between the first and second major side surfaces which afford passage of the cannula, the second major side surface having an adhesive adhered thereto for removably adhering the sheet to the skin of the patient;

an attachment means, associated with the distal surface of the anchor body and the first major side surface of the anchor sheet, for attaching the anchor body to the first major side surface of the anchor sheet, and wherein one of the first major side surface and the distal surface is a substantially planar surface and the other is a substantially curved surface.

* * * * *